United States Patent
Kirby et al.

(10) Patent No.: US 7,884,930 B2
(45) Date of Patent: Feb. 8, 2011

(54) INTEGRATED QUARTZ BIOLOGICAL SENSOR AND METHOD

(75) Inventors: Deborah Janice Kirby, Calabasas, CA (US); Randall Lynn Kubena, Oak Park, CA (US)

(73) Assignee: HRL Laboratories, LLC, Malibu, CA (US)

(*) Notice: Subject to any disclaimer, the term of this patent is extended or adjusted under 35 U.S.C. 154(b) by 0 days.

(21) Appl. No.: 12/145,678

(22) Filed: Jun. 25, 2008

(65) Prior Publication Data

US 2009/0147254 A1    Jun. 11, 2009

Related U.S. Application Data

(63) Continuation-in-part of application No. 11/818,797, filed on Jun. 14, 2007, and a continuation of application No. PCT/US2008/066660, filed on Jun. 12, 2008.

(51) Int. Cl.
*G01J 3/44* (2006.01)
(52) U.S. Cl. .................................... 356/301
(58) Field of Classification Search ............... 356/72, 356/73, 301; 438/49, 22–29, 32, 33, 48, 438/57, 64, 68, 74, 83, 98, 106–108, 116; 257/E21.002; 250/336, 389, 287, 306, 425
See application file for complete search history.

(56) References Cited

U.S. PATENT DOCUMENTS

| 3,766,616 A | 10/1973 | Staudte |
| 4,364,016 A | 12/1982 | Tanksi |
| 4,442,574 A | 4/1984 | Wanuga et al. |
| 4,618,262 A | 10/1986 | Maydan et al. |
| 4,870,313 A | 9/1989 | Hirama et al. ............. 310/320 |
| 4,944,836 A | 7/1990 | Beyer et al. ............... 156/645 |
| 5,260,596 A | 11/1993 | Dunn et al. |
| 5,552,016 A | 9/1996 | Ghanayem |
| 5,589,724 A | 12/1996 | Satoh et al. .................. 310/348 |
| 5,605,490 A | 2/1997 | Laffey et al. |
| 5,648,849 A | 7/1997 | Canteloup et al. |
| 5,658,418 A | 8/1997 | Coronel et al. |
| 5,666,706 A | 9/1997 | Tomita et al. |
| 5,668,057 A | 9/1997 | Eda et al. .................... 438/113 |
| 5,928,532 A | 7/1999 | Koshimizu et al. |
| 5,942,445 A | 8/1999 | Kato et al. |
| 5,981,392 A | 11/1999 | Oishi |

(Continued)

FOREIGN PATENT DOCUMENTS

EP    0 531 985 A1    3/1993

(Continued)

OTHER PUBLICATIONS

Abe, Takashi, et al., "One-chip multichannel quartz crystal microbalance (QCM) fabricated by Deep RIE," Sensors and Actuators, vol. 82, pp. 139-143 (2000).

(Continued)

*Primary Examiner*—Tarifur Chowdhury
*Assistant Examiner*—Abdullahi Nur
(74) *Attorney, Agent, or Firm*—Ladas & Parry

(57) ABSTRACT

A sensor integrates a quartz nanoresonator for mass detection and SERS for optical detection in a same cavity on a chip for redundancy in the detection of a species.

21 Claims, 11 Drawing Sheets

U.S. PATENT DOCUMENTS

| | | |
|---|---|---|
| 6,081,334 A | 6/2000 | Grimbergen et al. |
| 6,207,008 B1 | 3/2001 | Kijima |
| 6,297,064 B1 | 10/2001 | Koshimizu |
| 6,413,682 B1 | 7/2002 | Shibano et al. |
| 6,417,925 B1 | 7/2002 | Naya .......................... 356/445 |
| 6,424,418 B2 | 7/2002 | Kawabata et al. ........... 356/445 |
| 6,426,296 B1 | 7/2002 | Okojie |
| 6,432,824 B2 | 8/2002 | Yanagisawa |
| 6,514,767 B1 | 2/2003 | Natan |
| 6,614,529 B1 | 9/2003 | Tang |
| 6,627,067 B1 | 9/2003 | Branton et al. |
| 6,756,304 B1 | 6/2004 | Robert |
| 6,815,228 B2 | 11/2004 | Usui et al. |
| 6,862,398 B2 | 3/2005 | Elkind et al. |
| 6,933,164 B2 | 8/2005 | Kubena |
| 7,118,657 B2 | 10/2006 | Golovchenko et al. |
| 7,237,315 B2 | 7/2007 | Kubena et al. ................. 29/594 |
| 7,459,099 B2 | 12/2008 | Kubena et al. ................. 216/57 |
| 7,559,130 B2 | 7/2009 | Kubena et al. ................. 29/594 |
| 2002/0072246 A1 | 6/2002 | Goo et al. |
| 2002/0074947 A1 | 6/2002 | Tsukamoto |
| 2002/0185611 A1 | 12/2002 | Menapace et al. |
| 2003/0003608 A1 | 1/2003 | Arikado et al. |
| 2004/0065864 A1 | 4/2004 | Vogt et al. |
| 2006/0016065 A1 | 1/2006 | Nagaura |
| 2006/0252906 A1 | 11/2006 | Godschalx et al. ............. 528/86 |
| 2007/0205839 A1 | 9/2007 | Kubena et al. ............. 331/158 |
| 2008/0034575 A1 | 2/2008 | Chang et al. .................. 29/594 |
| 2008/0074661 A1* | 3/2008 | Zhang et al. ................ 356/301 |

FOREIGN PATENT DOCUMENTS

| | | |
|---|---|---|
| JP | 57-091017 | 6/1982 |
| JP | 04322507 A | 11/1992 |
| JP | 08330878 A | 12/1996 |
| JP | 2005-180921 A | 7/2005 |
| KR | 10-2001-0110428 A | 12/2001 |

OTHER PUBLICATIONS

Cleland, A.N., et al., "Fabrication of high frequency nanometer scale mechanical resonators from bulk Si crystals," Appl. Phys. Lett., vol. 69, No. 18, pp. 2653-2655 (Oct. 28, 1996).

Evoy, S., et al., "Temperature-dependent internal friction in silicon nanoelectromechanical systems," Applied Physics letters, vol. 77, No. 15, pp. 2397-2399 (Oct. 9, 2000).

Greer, J.A., et al., "Properties of SAW resonators fabricated on quartz substrates of various qualities," Ultrasonics Symposium, IEEE, vol. 1, pp. 31-36, (Nov. 1994).

Sirbuly, Donald J. et al., Multifunctional Nanowire Evanescent Wave Optical Sensors, Advanced Materials, 2007 (published online: Dec. 5, 2006), 19, pp. 61-66.

White, Lan M., et al., Increasing the Enhancement of SERS with Dielectric Microsphere Resonators, Spectroscopy-Eugene, Apr. 2006.

Yan, Fei, et al., "Surface-enhanced Raman scattering (SERS) detection for chemical and biological agents," IEEE Sensors Journal, vol. 5, No. 4, Aug. 2005.

* cited by examiner

PRIOR ART

INTEGRATED QUARTZ BIOLOGICAL SENSOR AND METHOD

RELATED APPLICATIONS

This is a Continuation-In-Part of U.S. patent application Ser. No. 11/818,797 filed on Jun. 14, 2007 and claims priority to PCT International Patent Application No. PCT/US2008/066660 filed on Jun. 12, 2008. This is a continuation of PCT/US2008/066660 filed on Jun. 12, 2008. Both applications are incorporated herein by reference.

This application may be related to U.S. patent application Ser. No. 10/426,931 titled "Quartz-Based Nanoresonators and Methods of Making Same" filed on Apr. 30, 2003; U.S. Pat. No. 6,933,164 titled "Method of Fabrication of a Micro-Channel Based Integrated Sensor For Chemical and Biological Materials" issued on Aug. 23, 2005 and U.S. Pat. No. 6,514,767 titled "Surface Enhanced Spectroscopy Active Composite Nanoparticles" issued on Feb. 4, 2003, all of which are incorporated by reference in their entirety.

TECHNICAL FIELD

The present disclosure relates to the detection of molecules, and more specifically to an device that integrates optical spectroscopy and a nanoresonator for detecting and monitoring biological molecules.

BACKGROUND

The need for detection of biological agents in a variety of applications is acute. The rapid detection of very small quantities of harmful molecules, DNA, viruses, etc. using inexpensive, disposable sensors is particularly important.

A number of methods have been developed that allow such detection. Microelectromechanical (MEMS) technology plays a major role in this field because MEMS sensors can be batch-processed for low cost and are capable of handling and detecting very small quantities of unknown substances. Small amounts of materials, often in the range of pico or femto liters, can be handled and measured.

Nanoresonators and microresonators are resonators that have linear dimensions on the order of nanometers and micrometers, respectively. Such silicon-based nanoresonators may have resonant frequencies as high as 600 MHz and a quality factor Q in the range of 1000-2000. Kubena et al (U.S. patent application Ser. No. 10/426,931) disclose a method for fabricating and integrating quartz-based nanoresonators on a high speed substrate for integrated signal processing by utilizing a combination of novel bonding and etching steps to form ultra thin quartz-based resonators with a resonant frequency in excess of 100 MHz.

Raman spectroscopy is commonly used to identify functional groups in a molecule. Surface enhanced Raman spectroscopy (SERS) provides enhanced detection capability permitting picomolar detection levels of chemical and biological species. In general, Raman spectroscopy provides real time detection of molecules in a non-contact mode, thereby avoiding sample contamination. Natan (U.S. Pat. No. 6,514,767 and U.S. Ser. No. 11/132,471) disclose a method for increasing the sensitivity of SERS for detection of known species with metal nanoparticle "tags" (nanotags).

For the detection of biological molecules, sensors in the prior art that may be sufficiently selective are not sensitive enough to monitor the presence of picomolar or nanomolar levels of a given molecule. On the other hand, highly sensitive sensors are not selective enough to discriminate at the molecular level, which is needed to differentiate various strains of bacteria. Therefore, a need continues to exist for small, easy to use sensors that offer high selectivity, high sensitivity, and sufficient accuracy for the monitoring of biological species.

SUMMARY

In one embodiment of the present disclosure, submicron-sized tags or labels can be uses as molecular or cellular optical tags by covalently or non-covalently affixing them to entities of interest that may range in size from molecules to macroscopic objects, for purposes of quantitation, location, identification, and/or tracking.

According to a first embodiment of the present disclosure, an apparatus is provided that includes a mass detector disposed within a cavity to detect a sample; and an optical Surface Enhanced Raman Spectroscopy (SERS) detector disposed within said cavity to detect said sample.

According to a second embodiment of the present disclosure, an apparatus is provided for detection and analysis of biological species comprising at least two silicon wafers, wherein the at least two silicon wafers comprise a mass detector and an optical Surface Enhanced Raman Spectroscopy (SERS) detector, wherein the optical SERS detector comprises a vertical cavity surface emitting laser (VCSEL), wherein the VCSEL is comprised of a lower metal contact, a first distributed Bragg reflector (DBR), an active layer comprised of one or more quantum wells, a second DBR and an upper metal contact; the apparatus further comprising an integrated beamsplitter and lens assembly coated with a dichroic filter, wherein the dichroic filter is comprised of thin films of varying refractive indices, a diffraction grating, and a detector array coated with a holographically formed filter.

According to a third embodiment of the present disclosure, a method for fabricating an apparatus is provided that includes providing a mass detector; an optical Surface Enhanced Raman Spectroscopy (SERS) detector; a first cavity, and a second cavity, wherein disposed on the first cavity is the mass detector for analyzing a molecule and disposed on the first and second cavity is the optical SERS detector for analyzing said molecule.

According to a fourth embodiment of the present disclosure, a method for fabricating a sensor includes providing a quartz substrate; providing at least one electrode and at least one tuning pad to the quartz substrate; providing a silicon handle wafer having a cavity etched therein; bonding the silicon handle wafer to the quartz substrate; thinning the quartz substrate; metallizing the quartz substrate; providing a silicon base wafer; providing a diffraction grating to the silicon base wafer; metallizing the silicon base wafer; bonding the quartz substrate to the silicon base wafer and subsequently removing the silicon handle wafer, thereby producing a resonator; removing quartz from the resonator thus obtaining a modified resonator; providing a cap silicon wafer having a cavity etched therein; providing a vertical cavity surface emitting laser (VCSEL) on the cap wafer; providing an integrated beamsplitter and lens assembly to the top surface of the cap wafer; providing a lens to the top surface of the cap silicon wafer; providing a detector array on the cavity of the cap wafer; inverting the cap wafer, and bonding the inverted cap wafer to the modified resonator.

The present disclosure relates to the integration of optical spectroscopy onto a nanoresonator for a sensitive means of selectively monitoring biological molecules. An apparatus and a method are disclosed for making an apparatus that is a sensor in which both mass detection using a quartz nanoresonator and optical detection using SERS is integrated onto at least one chip, thereby providing redundancy in detection of a species.

These and other features and advantages will become further apparent from the detailed description and accompanying figures that follow. In the figures and description, numerals indicate the various features, like numerals referring to like features throughout both the drawings and the description.

DETAILED DESCRIPTION

The present disclosure provides a sensor that integrates within a single device two separate and different detection and measurement functions: resonant spectroscopy and SERS. The resonant spectroscopy function is provided by a nanoresonator or microresonator, and the SERS by a simple Raman spectroscope. One novel concept disclosed herein is the recognition that the use of metal nanoparticles as nanotags in SERS can also be used to enhance the sensitivity of nanoresonators, as explained below with reference to FIG. 1.

Figure 1:
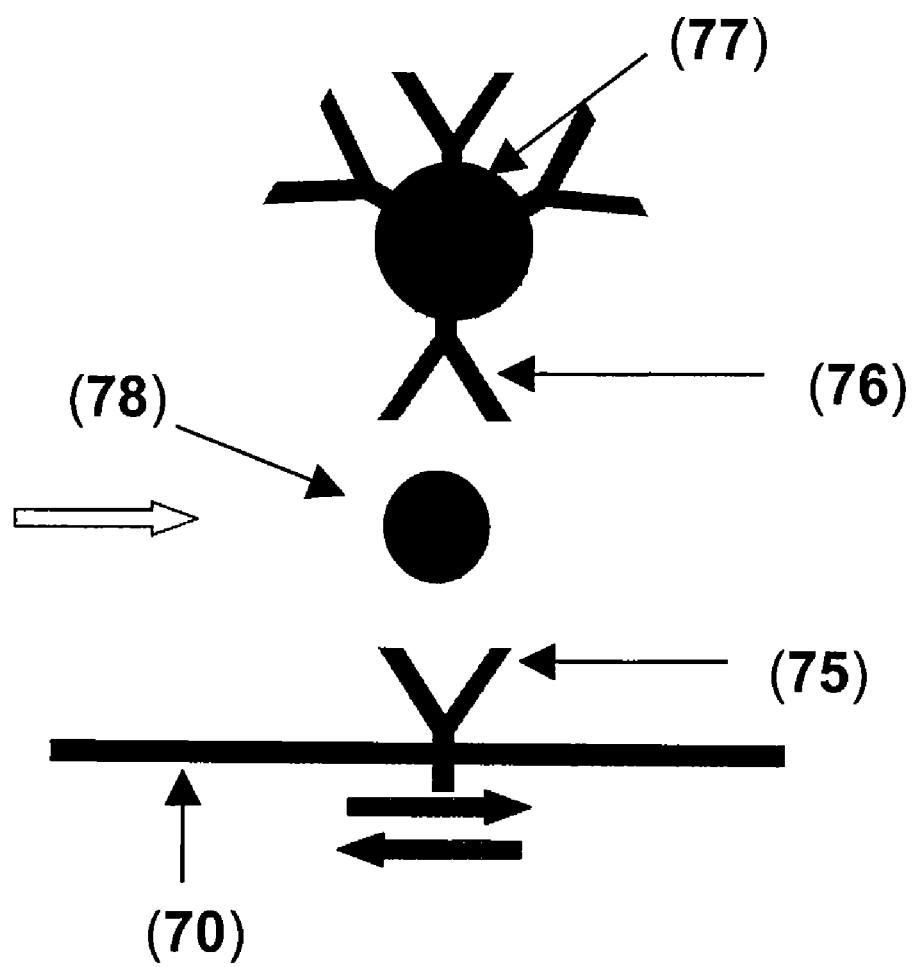
FIG. 1 is a schematic diagram illustrating the use of metal nanoparticles in detecting a molecule, as known in the prior art.

FIG. 1 illustrates the mechanism by which nanotags are used in SERS. A detection antibody 75 is applied to a surface 70. A molecule which is to be analyzed such as an antigen 78 is exposed to a nanoparticle 77 that has been complexed with cognate capture antibodies 76 (a "nanotag") to thereby complex with the antigen 78. The molecule-nanotag complex is then introduced in the presence of the surface 70, where the molecule also complexes with the detection antibody 75 on the surface. The detection antibody 75 is inherently specific to the required antigen detection, as is the capture antibody 76. The nanoparticles 77 have bonds specific for attachment to the capture antibody.

The present disclosure recognizes that such nanotags used in SERS also significantly increase the weight of the complexed molecule and thereby can be used to enhance the sensitivity of the resonant frequency shift of a nanoresonator by applying the detection antibodies 75 to a detection surface 70 of a nanoresonator as described elsewhere hereinbelow. A sensor according to the present disclosure thus offers SERS analysis on a cavity (e.g. chip wafer) along with mass detection, thereby providing an on-chip detection sensor that is both highly selective and sensitive as well as compact, lightweight, and economical enough to be disposable. To the applicants' knowledge this is the first biological sensor comprising SERS functionality and biological antibody detection using resonant frequency shifts at the microscale chip level.

Gold (Au) nanoparticles may be used in the preparation of nanotags to provide increased mass as well as SERS sensitivity. The principles involved in conducting SERS chemistry with Au nanoparticles as well as a method for attaching the nanoparticles to capture antibodies for Raman signal amplification have been previously described in U.S. Pat. No. 6,514,767 to Natan. In brief, Natan provides SERS-active composite nanoparticles (SACNs) that each comprise a SES-active metal nanoparticle, a submonolayer, monolayer, or multilayer of spectroscopy-active species in close proximity to the metal surface, and an encapsulating shell comprising a polymer, glass, or any other dielectric material. This arrangement places the spectroscopy-active molecule (alternately referred to herein as the "analyte" and is not to be confused with the species/molecule in solution that is ultimately being quantified) at the interface between the metal nanoparticle and the encapsulant. More specifically, SACNs are formed with a metal nanoparticle that has attached or associated with its surface one or more Raman-active molecules (alternately referred to herein as "analytes"). This complex of Raman enhancing metal and analyte(s) (referred to as a SERS-active metal nanoparticle) is then coated or encapsulated by an encapsulant. In a preferred embodiment the encapsulant is a glass material and the SACN is referred to as a glass-coated analyte loaded nanoparticle (GAN).

These SACNs are uniquely identifiable nanoparticles and can be used in virtually any situation in which it is necessary to label molecules or objects (including beads and other types of solid support) with an optical tag. Biomolecules can be conjugated readily to the exterior of SACNs by standard techniques, thereby allowing the particles to function as optical tags in biological assays. SACNs can be used in virtually any assay that uses an optical tag, such as a fluorescent label. However, as optical tags, SACNs have several distinct advantages over fluorescent labels, including vastly more sensitive detection, chemical uniformity, and the absolute resistance of the SERS activity to photobleaching or photodegradation. A further benefit of using SACNs as optical tags is the ease with which individual SACNs having different SERS-activities may be resolved from one another. At least twenty different SACNs are resolvable from one another using a simple Raman spectroscope. This enables multiplexed assays to be performed using a panel of different SACNs, each having a unique and distinguishable SERS-activity. In addition, SACNs can serve as novel "cleaveless" optical tags in bead-based combinatorial chemical syntheses. In this embodiment, each synthetic step in the scheme can be accompanied by the conjugation of a unique SACN to the bead. The reaction history of the bead, and hence the identity of the synthesized compound, can then be determined by reading the SERS spectrum of the bead, without first requiring that the SACNs are cleaved from the bead.

The resonant spectroscopy function contemplated herein is provided by a nanoresonator or microresonator such as a quartz nanoresonator as described in U.S. Pat. No. 6,933,164 to Kubena et al., along with the methodology for detecting amino assays at the chip (microscale) level with such micromachined resonators coated with detection antibodies. Kubena provides a wafer comprising a plurality of cantilever assemblies, each of the assemblies comprising a cantilever member and a micro-channel plate bonded to the cantilever member, where the micro-channel plate further comprises a micro-channel. Each of the cantilevers is functionalized by directing a flow of a plurality of functionalizing materials through the micro-channels, and dicing the wafer into a plurality of the sensors. Each of the cantilever assemblies includes a substrate with control and sense electrodes deposited on its top side and scribe marks etched on its back side, and a cantilever member having a cantilever, a seed layer and a contact pad formed on top side of the cantilever member. The micro-channel plate includes a micro-channel housing defining the micro-channel etched through the housing, and the back side of the cantilever member is bonded to the substrate and the micro-channel plate is bonded to said top side of the cantilever member. Control electronics are incorporated into the substrate for a completely integrated design.

To coat the antibodies on the micromachined resonators, a manifold is attached to the edge of the wafer of the nanoresonator and gases or liquid vapors that have gold-specific binding properties (e.g., sulfur or thiol group attachments) are allowed to flow through the microchannels and through the openings. These gases are then directed, on chip, to the appropriate cantilever, and the molecules will attach themselves to the gold seed layer located on top of each cantilever. Examples of the functionalizing materials include, but are not limited to, synthetic 5' thio-modified oligonucleotides with differing base sequences, E. coli serotypes, and siloxanes which will polymerize (after having adsorbed on the surface of gold), to form, for instance, polydimethylsiloxane, or an SOA bioassay detection film. In the present disclosure, the serotypes are instead antibodies linked to the gold seed layer. After functionalization, the manifold is removed and the wafer is ready for final dicing, after which the nano resonator is ready to perform as a sensor.

The operation of this sensor can be implemented in several standard modes. For example, the control electrode can be used to electrostatically excite the cantilevers at their resonant frequencies. This oscillation frequency can be observed and measured using the sense electrodes and capacitive detection. Differential changes in the mass of the cantilevers due to chemical exposure of the sensor and resulting complexing reactions with the functionalizing layers cause relative changes in the resonant frequencies of the cantilevers that are detected and measured.

Because each functionalizing layer can have a different chemical selectivity, the overall selectivity of the array may be higher than that of a single cantilever functionalized with only one molecule. Alternatively, chemical changes of the functionalizing layer can cause changes in the stress of the cantilevers and this relative change in stress between different cantilevers can be observed by detecting and measuring capacitive, piezoelectric, or piezo-resistive changes. As an additional measure, differential detection between coated and uncoated cantilevers is advantageous in eliminating temperature sensitivity. Finally, by incorporating on-chip resistive heaters, the sensor array can be re-activated by thermally desorbing the sensed material.

Figure 2:
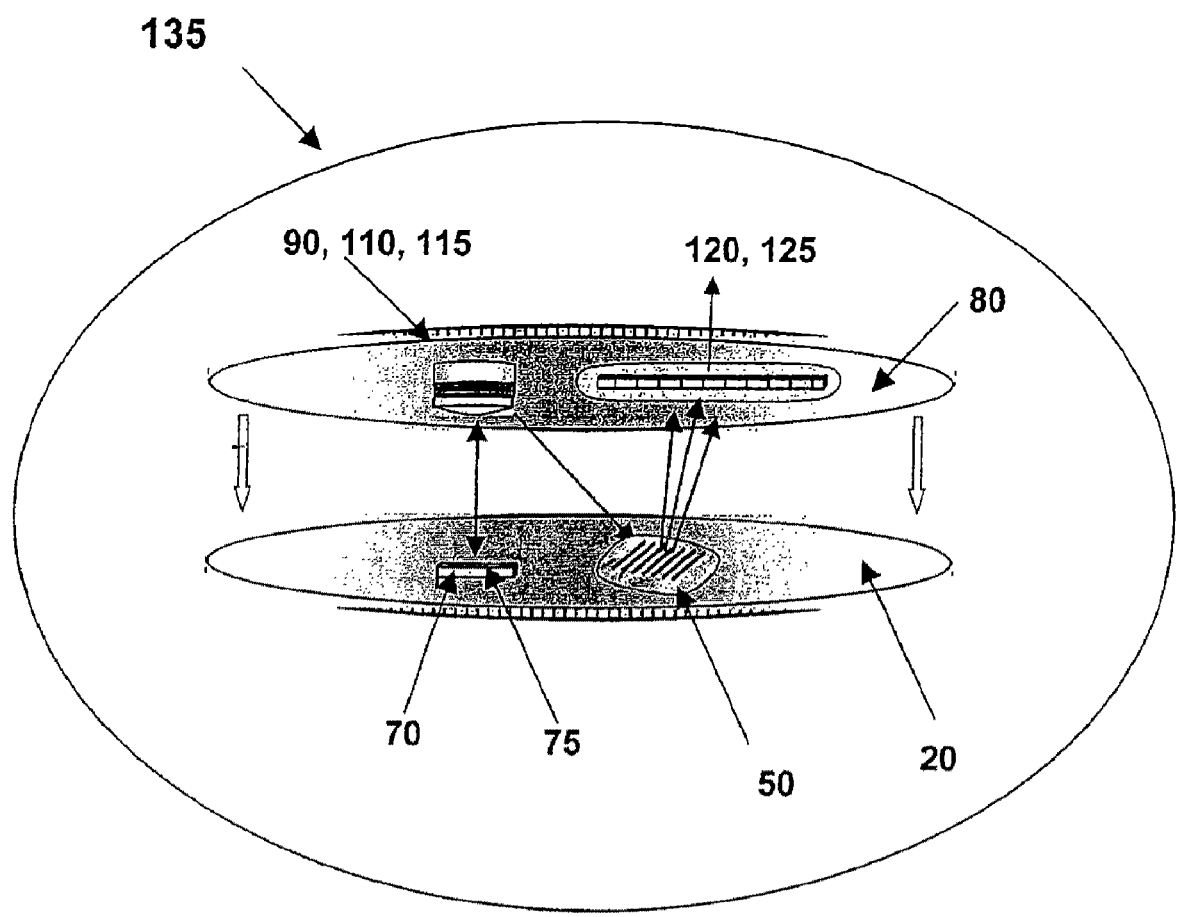
FIG. 2 is a schematic diagram of an integrated sensor according to the present disclosure.

With reference now to FIG. 2, one non-limiting embodiment of an integrated sensor apparatus 135 according to the present disclosure is formed of a base wafer 20 and a cap wafer 80 matched to the base wafer so that when assembled together, a cavity is defined therebetween to house the nanoresonator and the Raman spectroscope therein. As shown in the figure and described elsewhere herein, the base wafer includes the quartz nanoresonator and the cap wafer includes a NIR (near infra red) laser diode 90, a detector array 120, and holographic filter coating 125 that are part of the Raman spectroscope (see also FIGS. 4(a)-(q)). As previously described, the nanoresonator includes a resonator surface or region 70 with detection antibodies 75 attached thereto through a selective wet chemistry coating process that specifically only allows the antibodies to attach to the resonator region. As shown, the base wafer further includes a lithographically formed diffraction grating 50 that is coated with a thin film dichroic filter (more fully discussed elsewhere herein) for laser line rejection and forms the rest of the Raman spectroscope. The on-chip NIR (~800 nm) laser diode 90 is fabricated in an etched cavity on the cap wafer 80 and is coated with a thin film beam-splitter 110 and focusing lens assembly 115 (as also more fully discussed elsewhere herein). When the cap and base wafers are aligned and attached, the antibody coating 75 on the surface of the resonator 70 is disposed to be illuminated by the laser diode 90 and the wavelength resolution provided by the lithographically formed diffraction grating 50 as observed by the detector array 120 can be adjusted by changing the distance between the grating 50 and the detector array 120.

In use of a sensor according to the present disclosure, and still referring to FIG. 2, the chemical or biological agent (e.g. antigen) of interest, either in gas or liquid form, is exposed to the SACNs or to capture antibodies which are preferably complexed to metal nanoparticles, to complex therewith. The resulting liquid is then introduced into the sensor cavity where the agent will further complex with the detection antibodies on the resonator and thereby form a larger (detection antibody-antigen-capture antibody) complex on the sensor surface or region 70, thereby coating the nanoresonator with sandwich amino assays. This larger complex is then analyzed by resonant spectroscopy and simultaneously analyzed by the integrated SERS components (e.g. VSCEL 90, diffraction grating 50, and detector array 120).

For optical sensing (SERS), the diode laser beam 90 illuminates the surface of the resonator 70 and provides excitation for the SERS signal. Reflected light is directed, via beamsplitter 110, to periodic (diffraction) grating 50 for wavelength separation. As described elsewhere herein, a thin film dichroic filter 55 covers the grating 50 for the purpose of laser line rejection. The wavelength separated light is collected by the linear detector array 120 and its intensity versus wavelength is monitored. The detector array 120 is coated with a holographic filter 125 for rejection of Rayleigh scattering (unshifted light). In this manner a surface enhanced Raman signal that is characteristic of the antigen is detected, the amplitude of which is dependent on the concentration of the antigen species present. The SERS effect of a particular biological agent is known a priori and the observed discrete wavelength signals can thus be compared against the known SERS effect of various biological agents to identify the detected antigen.

Figure 3:
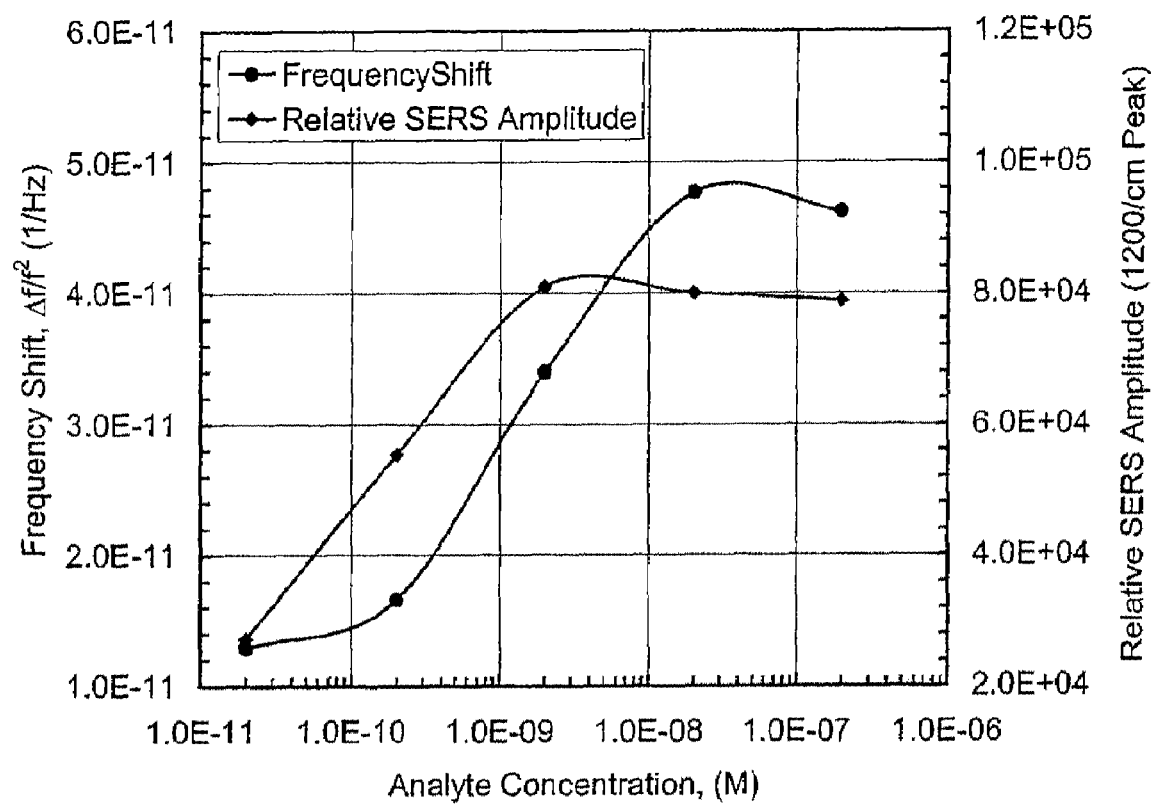
FIG. 3 is a graph presenting the dual measurements obtained with a nanoresonator according to the present disclosure.

In parallel with the SERS detection, the resonator (e.g., quartz nanoresonator) is driven at resonance and, as mass is added to the surface by the detection antibodies complexing with the biological agent-nanotag complexes, a shift in the resonant frequency of the resonator is observed. Results from simultaneous collection of mass added data and SERS data on a single quartz nanoresonator are shown in FIG. 3, which shows that the two sets of data are well correlated over a wide sensitivity range with a df/f² of $5\times10^{-1}$ $Hz^{-1}$ at a peak concentration of $9\times10^{-7}$ M. The corresponding relative SERS amplitude is $8.0\times10^4$ (for the 1200/cm peak). The ultimate sensitivity of the method disclosed herein is in the 100 s of femto-molar concentration.

Figure 4A:
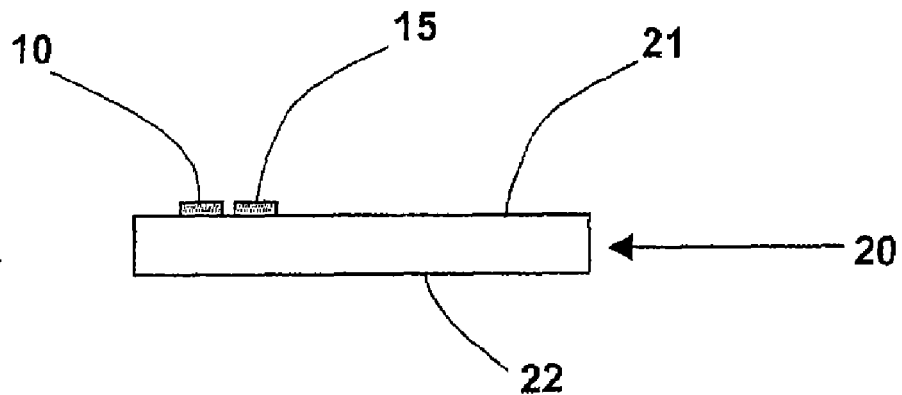
FIGS. 4(a)-(q) illustrate a method of manufacturing a nanoresonator according to the present disclosure.
Figure 4B:
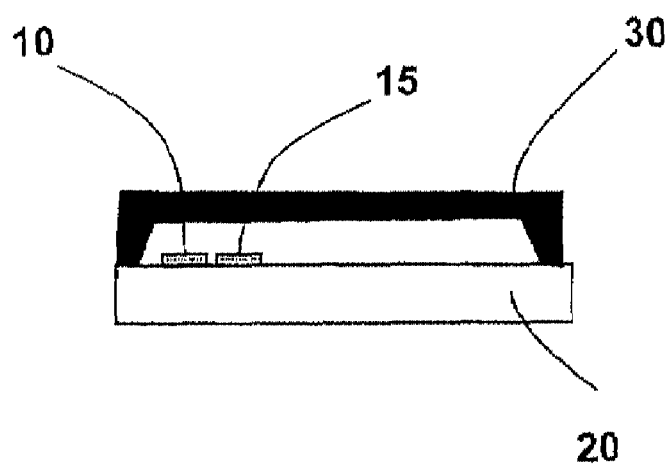
Figure 4C:
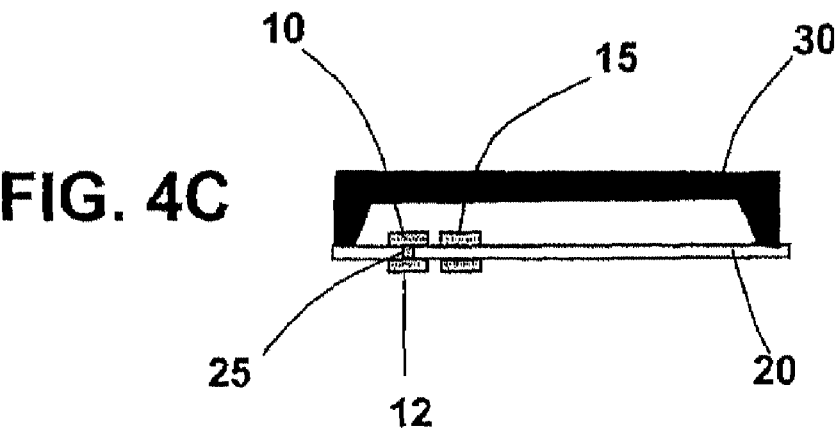
Figure 4D:
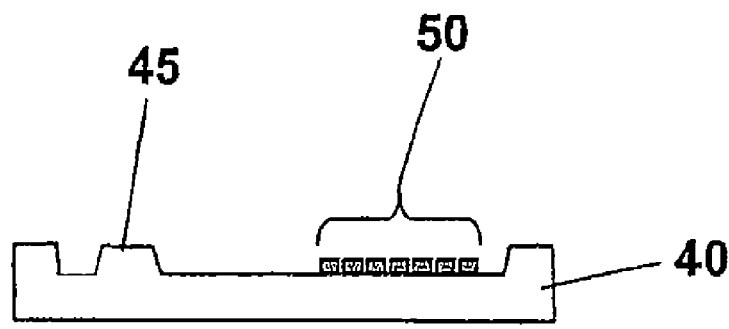
Figure 4E:
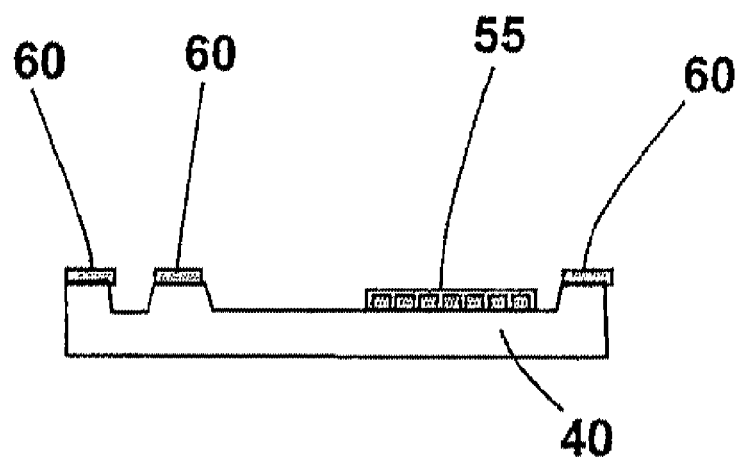
Figure 4F:
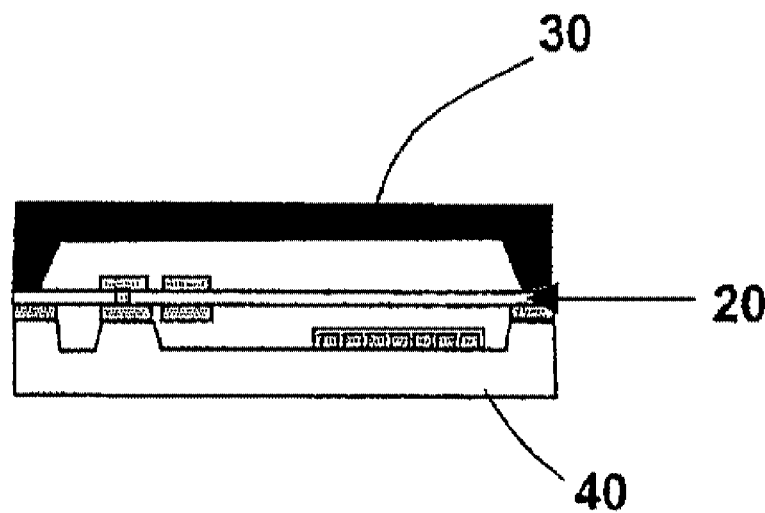
Figure 4G:
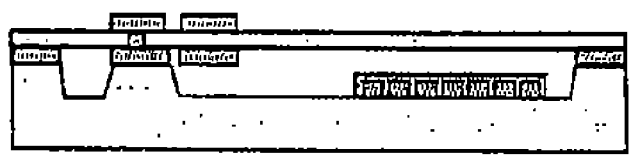
Figure 4H:
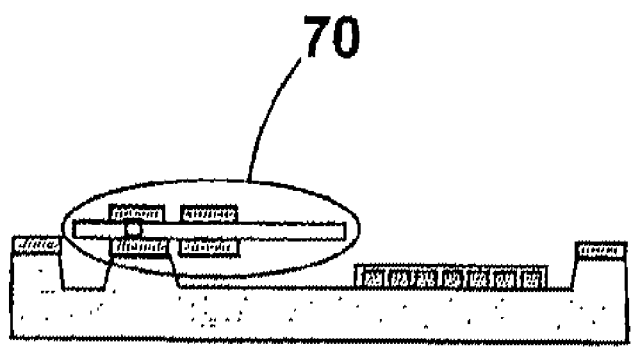
Figure 4I:
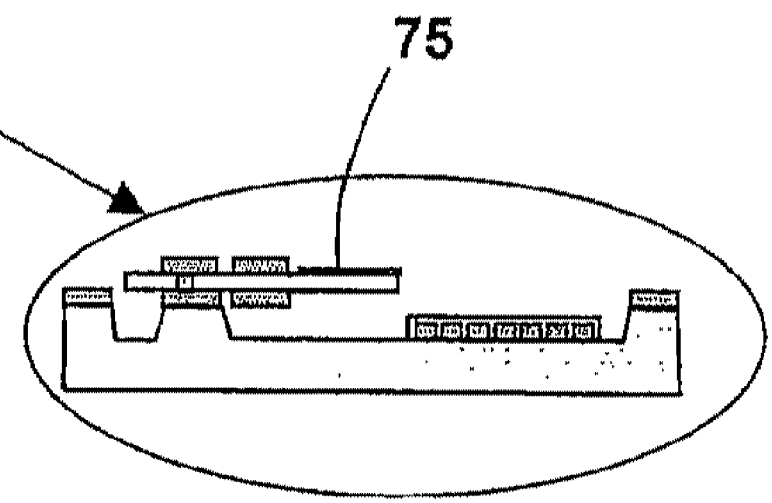
Figure 4J:
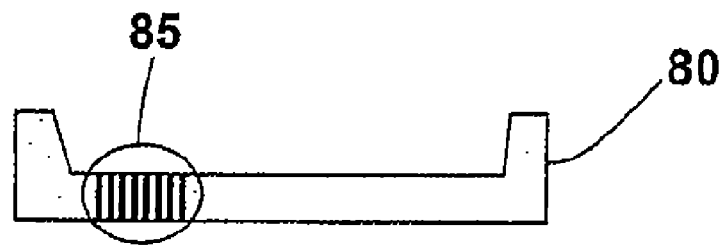
Figure 4K:
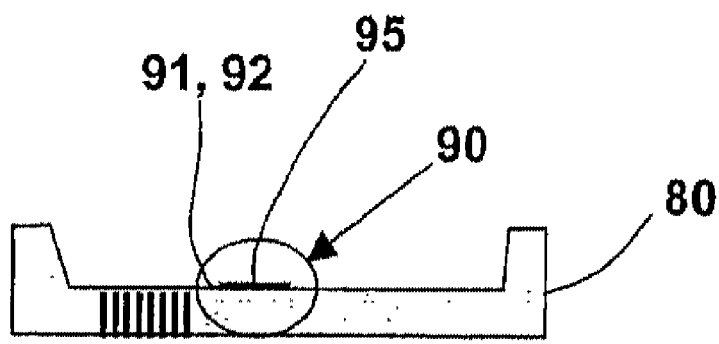
Figure 4L:
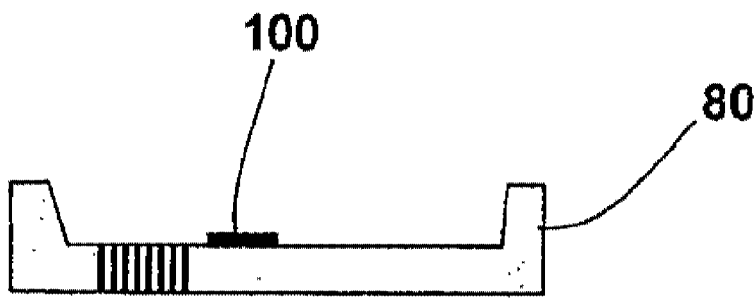
Figure 4M:
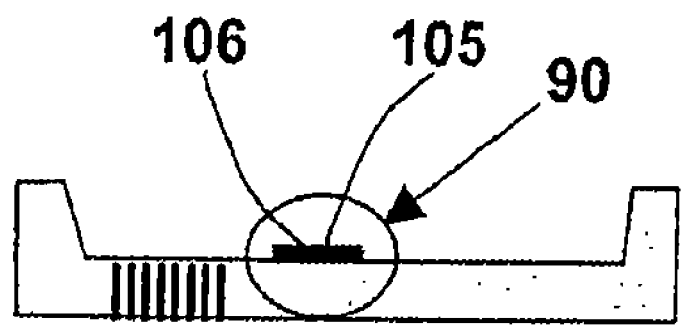
Figure 4N:
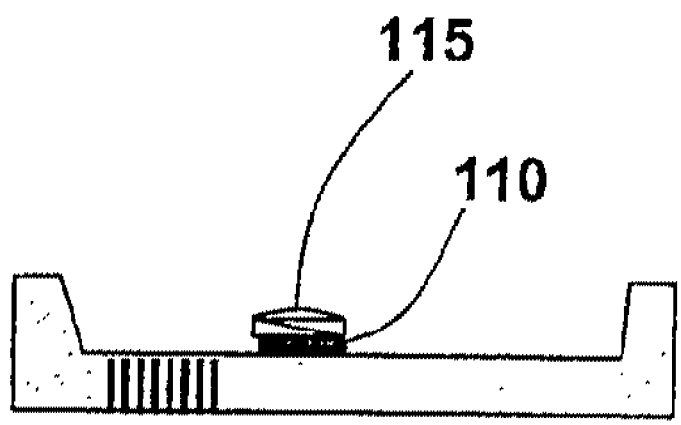
Figure 4O:
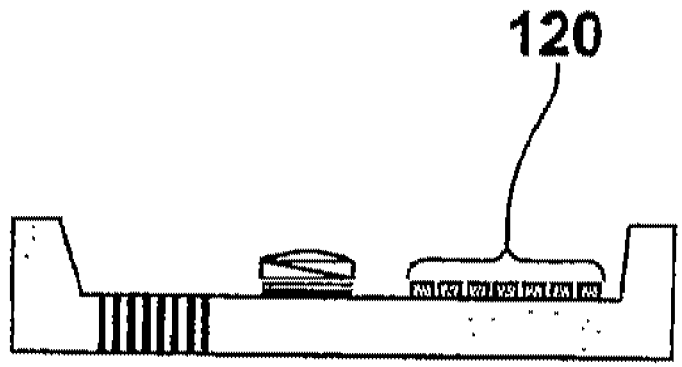
Figure 4P:
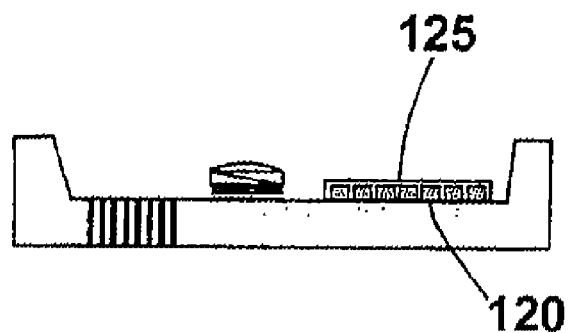
Figure 4Q:
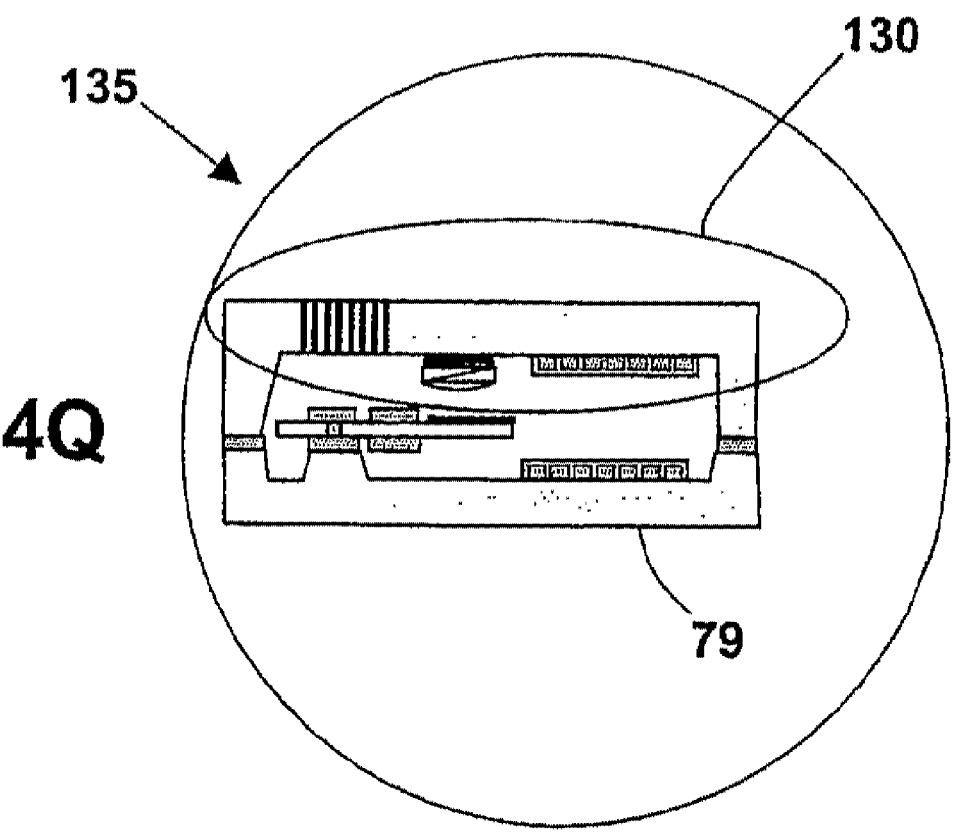
Figure 5A:
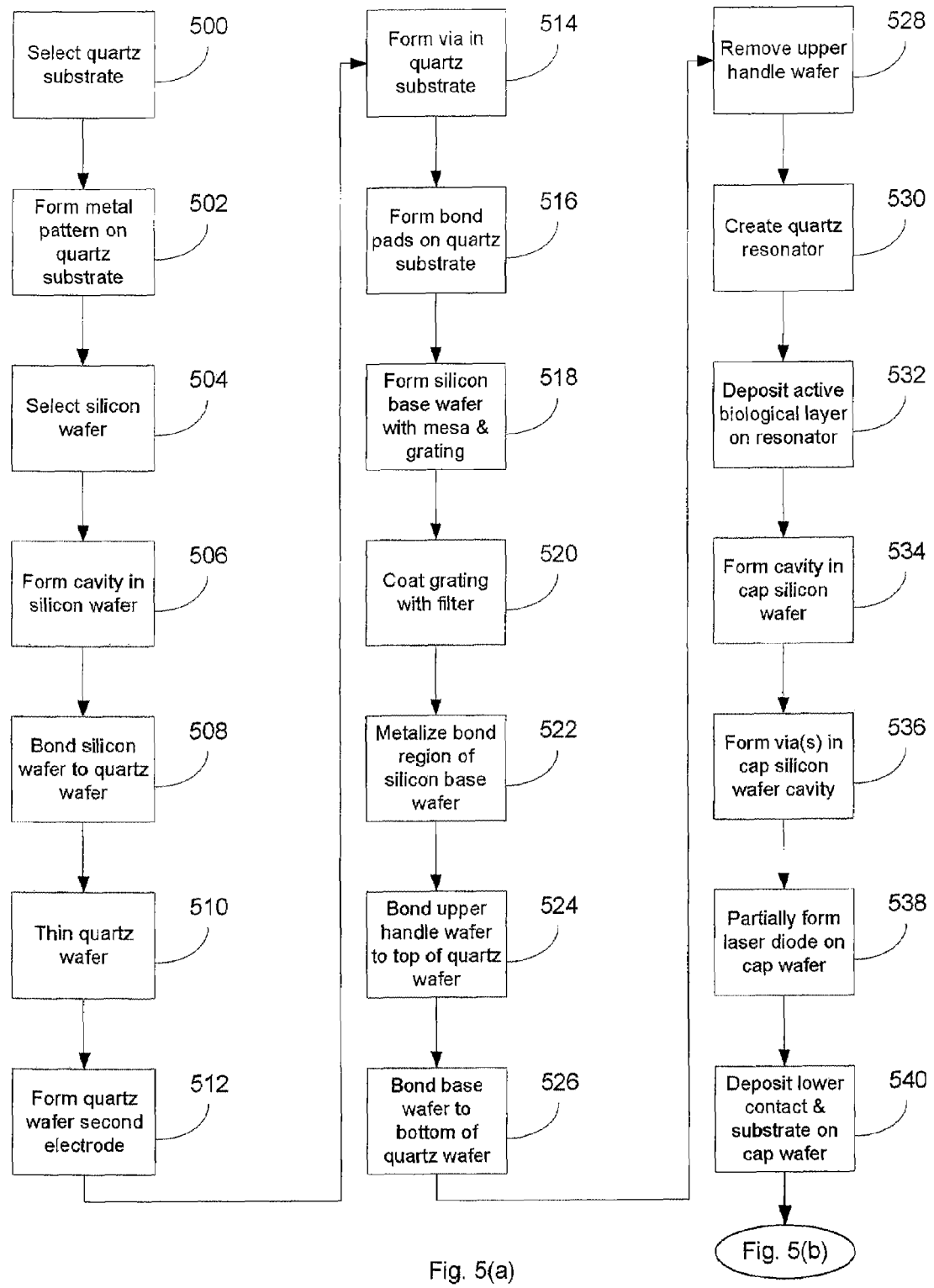
FIGS. 5(a)-(b) illustrate a flowchart for the method of FIG. 4.
Figure 5B:
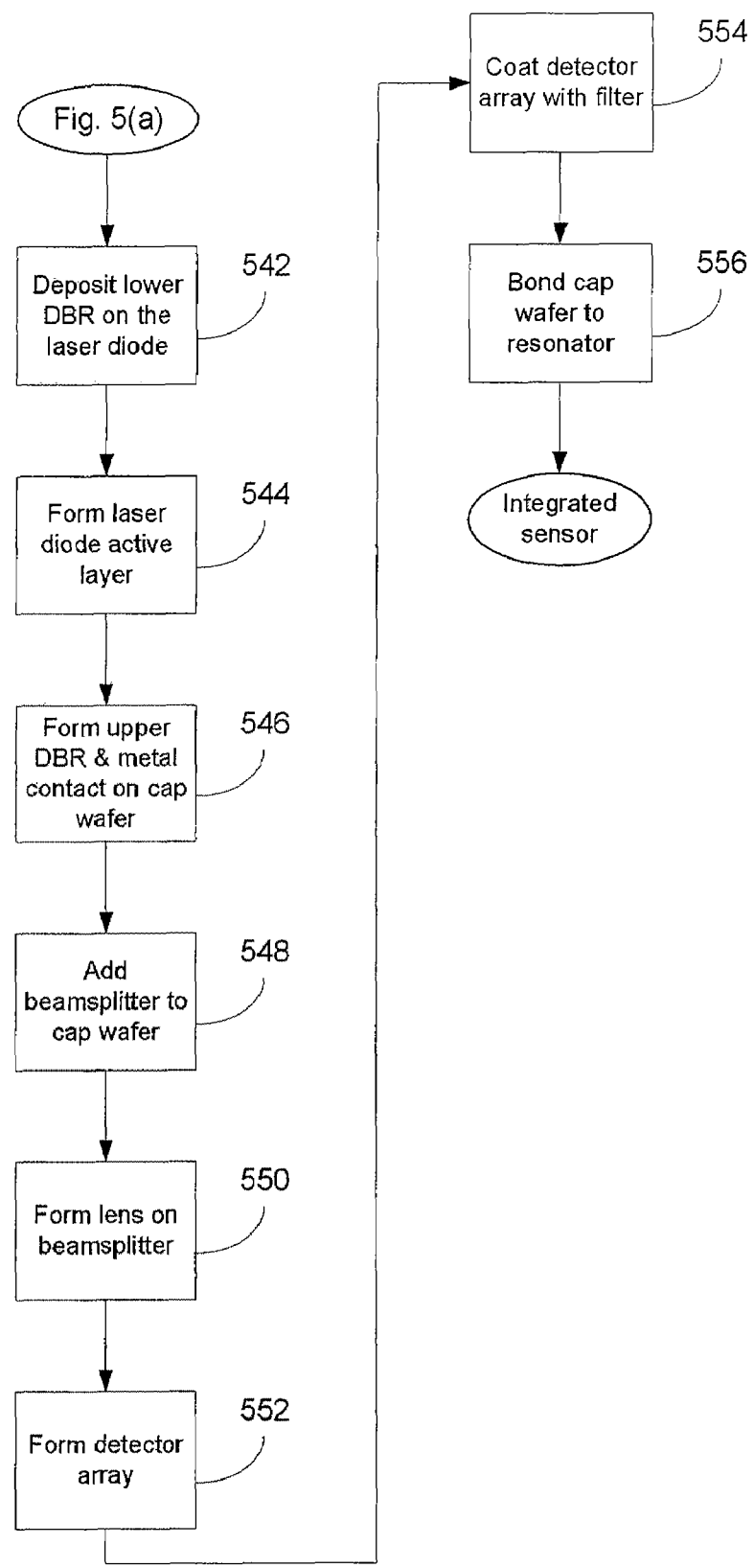

With reference now to FIGS. 4 and 5, one embodiment of a method for producing an integrated sensor according to the present disclosure begins with the selection 500 of a quartz substrate wafer 20 having a first surface 21 and a second surface 22 and the formation 502 of a metal pattern including a first electrode 10 and first tuning pad 15 onto the first surface, as illustrated in FIG. 4(a). A silicon wafer is next selected 504 and a cavity is formed 506 therein to thereby produce an upper silicon handle wafer 30 that is then bonded 508 to the first surface 21 of the quartz wafer 20 so as to enclose the first electrode 10 and first tuning pad 15 within the cavity, as illustrated in FIG. 4(b).

Referring to FIG. 4(c), the quartz wafer is next thinned 510 to the requisite resonator width (typically less than 10 micrometers). A second electrode 12 is next formed 512 on the second surface 22 of the quartz wafer and a via 25 is then formed and metalized 514 in the quartz wafer between the first electrode 10 on the first surface 21 and the second electrode 12. The quartz wafer is then metalized and patterned 516 for bond pads.

As shown in FIG. 4(*d*), a silicon base wafer 40 is next formed 518 with a lithographically etched mesa 45 and a lithographically etched diffraction grating 50 therein. As shown in FIG. 4(*e*), the diffraction grating 50 is then coated 520 with a dichroic filter 55 by layering thin films having varying refractive indices and thickness thereon. The bond region 60 of the silicon base wafer is subsequently metalized 522.

With reference to FIG. 4(*f*), in the next step the upper silicon handle wafer 30 is bonded 524 to the first surface of the quartz wafer 21 and the second surface of the quartz wafer 22 is bonded 526 to the silicon base wafer 40. As shown in FIG. 4(*g*), the upper silicon handle wafer 30 is then removed 528.

With reference to FIG. 4(*h*), the resonator region 70 is next protectively masked and all quartz except that under the masked regions is removed, thereby creating 530 a quartz resonator 79. An active biological layer 75 (e.g. detection antibodies) is next deposited 532 onto the surface of the resonator region as shown in FIG. 4(*i*).

As illustrated in FIG. 4(*j*), in the next step a cavity is formed 534 in a cap silicon wafer 80 and then at least one via 85 is formed 536 therethrough for exposure to antigens and capture antibodies. A laser diode such as a Vertical Cavity Surface Emitting Laser (VCSEL) 90 is then partially formed 538 on the cap wafer 80 and a lower metal contact 91 and n-type substrate 92 are deposited 540, as shown in FIG. 4(*k*). A lower distributed Bragg reflector (DBR) 95 is then deposited 542 on top of the laser diode by layering materials of varying refractive indices, each preferably with a thickness of these layers of $\lambda/4$.

Referring to FIG. 4(*l*), an active layer of the laser diode is next formed 544 in the form of a stack 100 of one or more quantum wells (QWs) that are formed by layering quantum wells and quantum well barrier materials. The stack of quantum wells is bounded by a confinement layer on either outer edge. As shown in FIG. 4(*m*), an upper (DBR) 105 and upper metal contact 106 are next formed 546 in the cap silicon wafer 80 to complete the laser diode. An integrated beamsplitter assembly 110 is then added 548 to the cap wafer and a lens 115 is formed 550 on the top surface of the beamsplitter assembly, as illustrated in FIG. 4(*n*).

The next step as illustrated in FIG. 4(*o*) entails forming 552 a detector array 120 on cavity floor of the cap silicon wafer 80, following which the detector array is coated 554 with a holographically formed filter 125 for rejection of Rayleigh scattering (unshifted light) as per FIG. 4(*p*). Finally, as shown in FIG. 4(*q*), the assembled cap wafer 130 is inverted and bonded 556 to the quartz resonator assembly 79 resulting in a combined mass detector and an optical Surface Enhanced Raman Spectroscopy (SERS) detector integrated onto a chip 135 as per the present disclosure.

As will be appreciated by the skilled person from the foregoing description, a sensor apparatus according to the present disclosure can be used in both gaseous and liquid environments and can thus be used to detect species in solution as well as those found in the air or any gaseous environment. Furthermore, such a sensor is rugged and can withstand the required chemical processing with no deleterious effects to its performance.

In accordance with the present disclosure, all optical and mechanical components of the sensor are fabricated on-chip. Given the small size and thinness of the resonator, the resonator can be exposed to a series of small volume solutions. In another embodiment, at least one microfluidic channel can be incorporated into the resonator to enable precise delivery and further reduce the volume required for the detection antibodies 75, or any other detection molecules. In an alternative embodiment, the resonator surface 70 can be submerged into solution for delivery of the detection antibodies 75.

In the embodiment of FIGS. 4 and 5, the NIR laser diode 90 is a VCSEL (Vertical Cavity Surface Emitting Laser) laser diode with a monolithic laser cavity in which the emitted light leaves the device in a direction perpendicular to the chip surface. The laser cavity is formed by the two semiconductor Bragg mirrors 95, 105 between which there is a gain region with several quantum wells 100 and a total thickness of a few microns. This VCSEL is less costly to manufacture in quantity, is easier to use, and is more efficient than other edge-emitting diodes presently available.

The detector array 120 on the cap wafer 80 may be made by a process that enables for micron-scale precision patterning of optical thin film dichroic coatings on a thin single substrate. Thus, thin film layers can be achieved through the deposition of thin layers of material onto a substrate, by physical vapor deposition such as evaporative or sputtering, or by a chemical process such as chemical vapor deposition.

According to a further embodiment of the present disclosure, the holographic filter coating 125 that is applied to the cap wafer of the resonator contains several layers that are recorded simultaneously within a thick stack, such that the optical density of the notch filter is high and its spectral bandwith can be extremely narrow. Furthermore, because their layering profile is sinusoidal instead of squarewave, holographic notch filters are free from extraneous reflection bands and provide significantly higher laser damage thresholds. A holographic filter as described is available from Kaiser Optical Systems, Inc. of Ann Arbor, Mich.

Preferred embodiments in accordance with the present disclosure are enumerated below.

Concepts

As short summaries, this writing has disclosed at least the following broad concepts:

Concept 1. An apparatus comprising:
  a mass detector disposed within a cavity to detect a sample; and
  an optical Surface Enhanced Raman Spectroscopy (SERS) detector disposed within said cavity to detect said sample.

Concept 2. The apparatus of concept 1, further comprising two wafers disposed to define the cavity therebetween.

Concept 3. The apparatus of concepts 1 or 2, wherein the mass detector is a quartz resonator.

Concept 4. The apparatus of concepts 1 or 2, wherein the mass detector is formed from a quartz substrate comprising a first surface and a second surface; the quartz substrate further comprising
  at least a first and second electrode;
  at least one tuning pad;
  at least one via, and
  a diffraction grating coated with a dichroic filter, wherein the first electrode is on the first surface and the second electrode is on the second surface, and the at least one via connects the first electrode and the second electrode.

Concept 5. The apparatus of any one of concepts 1-4, wherein the optical SERS detector comprises:
  a vertical cavity surface emitting laser (VCSEL), wherein the VCSEL comprises:
    a lower metal contact;
    a first distributed Bragg reflector (DBR);
    an active layer comprised of one or more quantum wells;
    a second DBR and an upper metal contact;
  the apparatus further comprising:
    an integrated beamsplitter and lens assembly coated with dichroic filter, wherein the dichroic filter is comprised of thin films of varying refractive indices;
    a diffraction grating, and
    a detector array coated with a holographically formed filter.

Concept 6. The apparatus of concept 5, wherein the VCSEL further comprises an n-type substrate.

Concept 7. The apparatus of any one of concepts 1-6, further comprising microfluidic channels connected to the mass detector for delivery of detection molecules.

Concept 8. A method for fabricating the apparatus of any one of concepts 1-7 comprising:
  providing a first cavity and a second cavity;
  providing a mass detector to the first cavity, and
  providing an optical SERS detector to the first and second cavity.

Concept 9. A method for fabricating a sensor comprising the steps of:
  providing a quartz substrate;
  providing at least one electrode and at least one tuning pad to the quartz substrate;
  providing a silicon handle wafer having a cavity etched therein;
  bonding the silicon handle wafer to the quartz substrate;
  thinning the quartz substrate;
  metallizing the quartz substrate;
  providing a silicon base wafer;
  providing a diffraction grating to the silicon base wafer;
  metallizing the silicon base wafer;
  bonding the quartz substrate to the silicon base wafer and subsequently removing the silicon handle wafer, thereby producing a resonator;
  removing quartz from the resonator thus obtaining a modified resonator;
  providing a cap silicon wafer having a cavity etched therein;
  providing a vertical cavity surface emitting laser (VCSEL) on the cap wafer;
  providing an integrated beamsplitter and lens assembly to the top surface of the cap wafer;
  providing a lens to the top surface of the cap silicon wafer;
  providing a detector array on the cavity of the cap wafer;
  inverting the cap wafer, and
  bonding the inverted cap wafer to the modified resonator.

Concept 10. The method of concept 9, wherein the quartz substrate comprises a first surface and a second surface;
  wherein the at least one electrode comprises a first electrode and a second electrode;
  the first electrode is positioned on the first surface of the quartz substrate and the second electrode is positioned on the second surface of the quartz substrate, and
  the quartz substrate further comprises at least one via, wherein the least one via connects the first electrode to the second electrode.

Concept 11. The method of concept 10, wherein the silicon handle wafer is bonded to the first surface of the quartz substrate.

Concept 12. The method of concepts 10 or 11, wherein the second surface of the quartz substrate is bonded to the silicon base wafer.

Concept 13. The method of any one of concepts 8-12, further comprising the step of coating said diffraction grating with a dichroic filter.

Concept 14. The method of any one of concept 8-13, further comprising the step of providing at least one via through the cavity of the cap silicon wafer.

Concept 15. The method of any one of concepts 8-14, further comprising the step of providing a holographically formed filter coat to the detector array.

Concept 16. The method of any one of concepts 8-15, further comprising the step of coating the modified resonator with antibodies.

Concept 17. The method of concept 16, wherein the antibodies are provided by way of at least one microfluidic channel.

Concept 18. The method of concept 16, wherein the antibodies are provided by submerging the modified resonator into solution.

Concept 19. The apparatus of any one of concepts 1-7 for use in detecting biological species.

Concept 20. The apparatus made by the method of any one of concepts 8-18 for use in detecting biological species.

Let it be understood that the foregoing description is only illustrative of the invention. Various alternatives and modifications can be devised by those skilled in the art without departing from the spirit of the invention. Specifically, the wafers could be made of material other than silicon. Accordingly, the present invention is intended to embrace all such alternatives, modifications, and variances which fall within the scope of the appended claims. Additionally, whenever multiple steps are recited in a claim, it is intended that the order of some or all of the steps can be different from the order shown in the claim

What is claimed is:

1. An apparatus comprising:
  a mass detector disposed within a cavity to detect a sample in said cavity; and
  an optical Surface Enhanced Raman Spectroscopy (SERS) detector disposed within said cavity to detect said sample.

2. The apparatus of claim 1, further comprising two wafers disposed to define the cavity therebetween.

3. The apparatus of claim 1, wherein the mass detector is a quartz resonator.

4. The apparatus of claim 1, wherein the mass detector is formed from a quartz substrate comprising a first surface and a second surface; the quartz substrate further comprising
  at least a first and second electrode;
  at least one tuning pad;
  at least one via, and
  a diffraction grating coated with a dichroic filter,
  wherein the first electrode is on the first surface and the second electrode is on the second surface, and the at least one via connects the first electrode and the second electrode.

5. The apparatus of claim 1, wherein the optical SERS detector comprises:

a vertical cavity surface emitting laser (VCSEL), wherein the VCSEL comprises:
a lower metal contact;
a first distributed Bragg reflector (DBR);
an active layer comprised of one or more quantum wells;
a second DBR and an upper metal contact;
the apparatus further comprising:
an integrated beamsplitter and lens assembly coated with dichroic filter, wherein the dichroic filter is comprised of thin films of varying refractive indices;
a diffraction grating, and
a detector array coated with a holographically formed filter.

6. The apparatus of claim 5, wherein the VCSEL further comprises an n-type substrate.

7. The apparatus of claim 1, further comprising microfluidic channels connected to the mass detector for delivery of detection molecules.

8. A method for fabricating the apparatus of claim 1 comprising:
providing a first cavity and a second cavity;
providing a mass detector to the first cavity, and
providing an optical SERS detector to the first and second cavity.

9. The apparatus of claim 1 for use in detecting biological species.

10. The apparatus of claim 1, wherein the mass detector includes a resonator with an antibody coating disposed thereon.

11. A method for fabricating a sensor comprising the steps of:
providing a quartz substrate;
providing at least one electrode and at least one tuning pad to the quartz substrate;
providing a silicon handle wafer having a cavity etched therein;
bonding the silicon handle wafer to the quartz substrate;
thinning the quartz substrate;
metallizing the quartz substrate;
providing a silicon base wafer;
providing a diffraction grating to the silicon base wafer;
metallizing the silicon base wafer;
bonding the quartz substrate to the silicon base wafer and subsequently removing the silicon handle wafer, thereby producing a resonator;
removing quartz from the resonator thus obtaining a modified resonator;
providing a cap silicon wafer having a cavity etched therein;
proving a vertical cavity surface emitting laser (VCSEL) on the cap wafer;
proving an integrated beamsplitter and lens assembly to the top surface of the cap wafer;
providing a lens to the top surface of the cap silicon wafer;
providing a detector array on the cavity of the cap wafer;
inverting the cap wafer, and
bonding the inverted cap wafer to the modified resonator.

12. The method of claim 11, wherein the quartz substrate comprises a first surface and a second surface;
wherein the at least one electrode comprises a first electrode and a second electrode;
the first electrode is positioned on the first surface of the quartz substrate and the second electrode is positioned on the second surface of the quartz substrate,
and
the quartz substrate further comprises at least one via, wherein the least one via connects the first electrode to the second electrode.

13. The method of claim 12, wherein the silicon handle wafer is bonded to the first surface of the quartz substrate.

14. The method of claim 12, wherein the second surface of the quartz substrate is bonded to the silicon base wafer.

15. The method of claim 11, further comprising the step of coating said diffraction grating with a dichroic filter.

16. The method of claim 11, further comprising the step of providing at least one via through the cavity of the cap silicon wafer.

17. The method of claim 11, further comprising the step of providing a holographically formed filter coat to the detector array.

18. The method of claim 11, further comprising the step of coating the modified resonator with antibodies.

19. The method of claim 18, wherein the antibodies are provided by way of at least one microfluidic channel.

20. The method of claim 18, wherein the antibodies are provided by submerging the modified resonator into solution.

21. The apparatus made by the method of claim 11 for use in detecting biological species.

* * * * *